US008822432B2

(12) United States Patent
Oe et al.

(10) Patent No.: US 8,822,432 B2
(45) Date of Patent: Sep. 2, 2014

(54) EQUOL PRODUCTION ACCELERATING COMPOSITION

(75) Inventors: Kenichi Oe, Uji (JP); Takashi Kimura, Uji (JP)

(73) Assignee: Unitika Ltd., Amagaski-Shi (JP)

(*) Notice: Subject to any disclaimer, the term of this patent is extended or adjusted under 35 U.S.C. 154(b) by 381 days.

(21) Appl. No.: 12/304,301

(22) PCT Filed: Jun. 15, 2007

(86) PCT No.: PCT/JP2007/062164
§ 371 (c)(1),
(2), (4) Date: Dec. 11, 2008

(87) PCT Pub. No.: WO2007/148631
PCT Pub. Date: Dec. 27, 2007

(65) Prior Publication Data
US 2009/0233880 A1      Sep. 17, 2009

(30) Foreign Application Priority Data

Jun. 20, 2006   (JP) ................................ 2006-170202

(51) Int. Cl.
*C07H 3/04*       (2006.01)
*A61K 31/7016*    (2006.01)
*A61K 31/7012*    (2006.01)

(52) U.S. Cl.
CPC .............. *C07H 3/04* (2013.01); *A61K 31/7016* (2013.01); *A61K 31/7012* (2013.01)
USPC ...................................... 514/53; 536/123.12

(58) Field of Classification Search
None
See application file for complete search history.

(56) References Cited

U.S. PATENT DOCUMENTS

| 5,663,377 A | 9/1997 | Curley, Jr. et al. |
| 2004/0147594 A1 | 7/2004 | Setchell et al. |
| 2005/0171194 A1 | 8/2005 | Yu et al. |
| 2007/0190115 A1 | 8/2007 | Kimura et al. |
| 2010/0022463 A1 | 1/2010 | Kimura et al. |

FOREIGN PATENT DOCUMENTS

| CN | 1265596 A | 9/2000 |
| CN | 1682764 A | 10/2005 |
| EP | 1 025 850 A1 | 8/2000 |
| EP | 1510521 A1 | 3/2005 |
| JP | 5-284939 A | 11/1993 |
| JP | 07-252156 A | 10/1995 |
| JP | 7-277991 A | 10/1995 |
| JP | 10-56959 A | 3/1998 |
| JP | 3501237 B2 | 12/2003 |
| JP | 3559063 B2 | 8/2004 |
| JP | 2005-232074 A | 9/2005 |
| JP | 2006143623 A | 6/2006 |
| JP | 2007-116972 A | 5/2007 |
| WO | 2005-000042 A1 | 1/2005 |
| WO | 2005/074708 A1 | 8/2005 |
| WO | 2006-013929 A1 | 2/2006 |
| WO | 2006028929 A1 | 3/2006 |
| WO | WO2008/153945 | * 12/2008 ............. A61K 31/55 |

OTHER PUBLICATIONS

"Definition of derivertive", retrieved from Merriam-Webster online dictionary <<http://www.merriamwebster.com/dictionary/derivative>> on Apr. 6, 2011, 2 pages.*
Gove et al., Webster's Third New International Dictionary, 1963, p. 1798.*
"Osteoporosis", Merck Manual Online Edition, [retrieved on May 11, 2011]. Retrieved from the Internet http://www.merckmanuals.com/home/print/sec05/ch060/ch060a.html. Revision Feb. 2008.*
"Breast Cancer", Merck Manual Online Edition, [retrieved on May 11, 2011]. Retrieved from the Internet http://www.merckmanuals.com/home/print/sec22/ch251/ch251f.html. Revision Nov. 2008.*
Upadhya et al., Hepatology, 2000, 31, p. 1115-1122.*
Rasmussen et al., Pharmacol. Ther., 1997, 75, 69-75.*
Saitoh et al., Biosci. Biotechnol. Biochem., 2001, 65, 2220-2225.*
Calcium-sandoz, retrieved on Dec. 29, 2011 from STN database, 2 pages.*
USDA Database for the Isoflavone Content of Selected Foods, Release 2.0, Prepared by Bhagwat et al., (Sep. 2008) pp. i and 1-49.*
Chinese Office Action issued on Feb. 16, 2011 in the corresponding Chinese Patent Application No. 200780022474.4.

(Continued)

*Primary Examiner* — Eric S Olson
(74) *Attorney, Agent, or Firm* — Sughrue Mion, PLLC

(57) ABSTRACT

A composition which can significantly accelerate equol production is provided. When formulated in a pharmaceutical preparation or a food or drink, this composition exerts effects of preventing a vascular disease by the cholesterol lowering function, preventing breast cancer or prostatic cancer, and preventing and/or treating osteoporosis. Also, when formulated in a feed or a pet food, the bone density is enhanced, so that it exerts effects to prevent weak legs of a pig, to strengthen egg shell of a laying hen, to prevent osteoporosis in a dog etc., and the like. It is a composition which comprises lactobionic acid, a salt of lactobionic acid or lactobionolactone as an active ingredient and a food or drink, a feed, a pet food or a pharmaceutical preparation, which contains the composition, and have effects to prevent and treat osteoporosis, an function to increase bone density, an effect to prevent breast cancer or prostatic cancer, and a cholesterol lowering function.

4 Claims, 1 Drawing Sheet

(56) References Cited

OTHER PUBLICATIONS

Jensen, Lars Bjorn et. al. : "Bone mineral changes in obese women during a moderate weight loss with and without calcium supplementation" Journal of Bone and Mineral Research, vol. 16, No. 1, Jan. 2001, pp. 141-147, XP002588518 ISSN: 0884-0431.

Miocinovic, Ranko et. al. : "In vivo and in vitro effect of baicalein on human prostate cancer cells" International Journal of Oncology, Demetrios A. Spandidos Ed. & Pub, GR, vol. 26, No. 1, Jan. 2005, pp. 241-246, XP009104223 ISSN: 1019-6439.

Extended European search report dated Jul. 12, 2010, issued by the European Patent Office in counterpart European Application No. 07745418.9-2123.

Fujioka, M. et al., *Equol, a Metabolite of Daidzein, Inhibits Bone Loss in Ovariectomized Mice*, The Journal of Nutrition, 2004, pp. 2623-2627.

Akaza, H. et al., *Is Diadzein Non-metabolizer a High Risk for Prostate Cancer? A Case-controlled Study of Serum Soybean Isoflavone Concentration*, Jpn. J. Clin. Oncol., 2002, vol. 32, No. 8, pp. 296-300.

Duncan, A. et al., *Premenopausal Equol Excretors Show Plasma Hormone Profiles Associated with Lowered Risk of Breast Cancer*, Cancer Epidemiology, Biomarkers & Prevention, 2000, vol. 9, pp. 581-586.

Yoshiko Ishimi, "Daizu Isoflovone-Kotsuso Shosho no Yobo o Chushin ni-", Rinsho Eiyo, 106 (5), pp. 593-599, 2005.

Motoi Tamura, "Isoflavone o Taisha suru Chonai Saikin Kinosei Seibun Equol Seisan ni Kanyo?", Kagaku to Seibutsu, 44 (3), pp. 151 to 153, vol. 44, No. 3; Mar. 2006.

Kazuhiko Kato, et al. "Daizu Tanpakushitsu Kankyu (Soybean Protein Studies)", Fuji Foundation for Protein Research, vol. 5 pp. 134-137, Oct. 2002.

Abstract of 49th Annual Meeting of Japan Society for Bioscience, Biotechnology and Agrochemisty, published by Japan Society for Bioscience, Biotechnology, and Agrochemisty; p. 97, 2005.

Abstract of the 56th Annual meeting of Japanese Society of Nutrition and Food Science, published by Japanese Society of Nutrition and Food Science, p. 138, 2002.

Communication from the Japanese Patent Office dated Apr. 23, 2012, in a counterpart application No. 2006-170202.

Office Action dated Nov. 2, 2012, issued by the State Intellectual Property Office of the People's Republic of China in Chinese Patent Application No. 200780022474.4.

Decision on Rejection dated May 6, 2013 issued by the State Intellectual Property Office of the People's Republic of China in Chinese Patent Application No. 200780022474.4.

\* cited by examiner

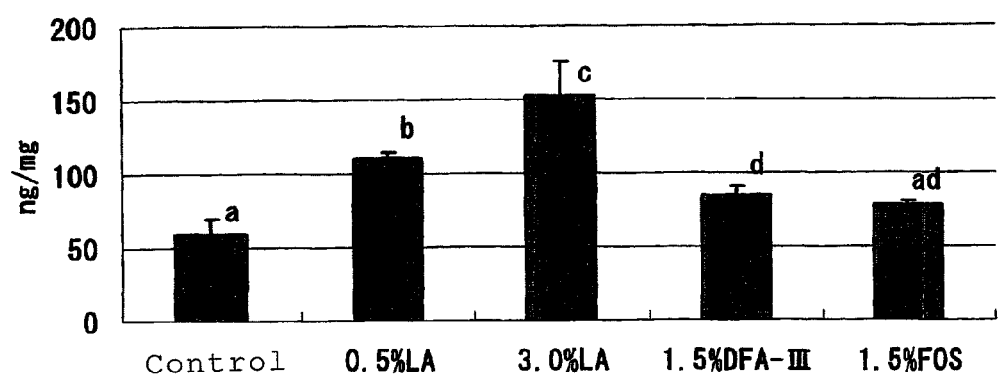

EQUOL PRODUCTION ACCELERATING COMPOSITION

TECHNICAL FIELD

The present invention relates to an equol production accelerating composition, which is used in a food or drink, a feed, a medicine and the like, and from which effects such as acceleration of equol production in the intestines, and improvement of the bone density can be obtained when ingested.

BACKGROUND OF THE INVENTION

Accompanying the advance of an aging society, osteoporosis, which reduces bone density and contributes to easy bone fracture with the advance of age, is becoming a serious problem. It has been revealed that osteoporosis causes a fracture of lumber vertebra or thighbone due to reduction of the bone mineral content and thereby becomes a cause for bedridden state. Particularly, females are apt to get osteoporosis due to rapid reduction of the bone mineral content caused by the estrogen secretion reduction with menopause. Regarding the treatment of osteoporosis, since it is not easy to restore the once reduced bone mineral content, it is considered to be very important to prevent osteoporosis from a younger age or to prevent the rapid reduction of the bone mineral content after menopause.

In order to prevent osteoporosis, it is important to increase bone mass from a younger stage, and for this purpose, it is necessary to take care of appropriate physical exercise and daily ingesting foods. In having meals, it is important to ingest much dairy products and fishes which are rich in calcium. In addition, use of vitamin K (e.g., see Patent Reference 1), oligosaccharides and minerals (e.g., see Patent Reference 2), casein phosphopeptide (e.g., see Patent Reference 3), soybean isoflavone (e.g., see Non-patent Reference 1) or vitamin D and the like as so-called healthy food, has been recommended recently as they are effective.

Particularly, equol, which is a metabolite of a kind of soybean isoflavone, daidzein, is isoflavones having various characteristics such as a high antioxidant activity and a high estrogen activity, and has already been disclosed as an agent for treating osteoporosis (Patent Reference 4). In addition, as the functions of equol, a plasma cholesterol lowering function, suppression of breast cancer or prostatic cancer and the like have been reported (Non-patent Reference 2).

However, since the metabolism from daidzein to equol is mainly carried out by intestinal bacteria, it is known that the metabolism is largely influenced by individual intestinal bacterial flora and the production quantity varies with the difference in sex and the difference in the human race. Actually, it has been reported that approximately from 60 to 70% of Europeans and Americans have a low ability to produce equol. Accordingly, DFA III (difructose-dianhydride III) (Non-patent Reference 3) and a fructo-oligosaccharide (Non-patent Reference 4) have so far been known as the substances which accelerate production of equol.

Patent Reference 1: JP-A-10-056959
Patent Reference 2: JP-A-7-252156
Patent Reference 3: JP-A-5-284939
Non-patent Reference 1: "Daizu Tanpakushitsu Kenkyu (Soybean Protein Studies)", written by Kazuhiko Kato and Hiromi Suemitsu, published by Fuji Foundation for Protein Research, Vol. 5, p. 134-137 (2002)
Patent Reference 4: JP-A-2005-232074
Non-patent Reference 2: "Kagaku To Seibutsu (Chemistry and Biology)", published by Japan Society for Bioscience, Biotechnology and Agrochemistry, Vol. 44, No. 3, p. 151-153 (2006)
Non-patent Reference 3: Abstract of the 49th Annual Meeting of Japan Society for Bioscience, Biotechnology and Agrochemistry, published by Japan Society for Bioscience, Biotechnology and Agrochemistry, p. 97 (2005)
Non-patent Reference 4: Abstract of the 56th Annual Meeting of Japanese Society of Nutrition and Food Science, published by Japanese Society of Nutrition and Food Science, p. 138 (2002)

DISCLOSURE OF THE INVENTION

Problems that the Invention is to Solve

Although the fructo-oligosaccharide and DFA III can increase production of equol, the effect is insufficient, and a food material which can efficiently accelerate production of equol has not been developed yet.

In addition, equol is not contained in foods and is expensive because the equol on the market is available only as a reagent. Thus, there is no way to ingest equol itself at low cost and easily. Accordingly, demands have been directed toward the development of a food material which accelerates equol production significantly.

The present invention aims at providing a composition which can accelerate equol production significantly.

Means for Solving the Problems

With the aim of solving such problems, the present inventors have conducted extensive studies, and as a result, found that the equol concentration in blood is significantly increased by ingesting a composition which contains an aldonic acid or a derivative thereof as an active ingredient, preferably a composition that contains, as the aldonic acid or the derivative thereof, lactobionic acid, a salt of lactobionic acid or lactobionolactone as an active ingredient, thus resulting in the accomplishment of the present invention.

That is, the gist of the present invention resides in an equol production accelerating composition, which comprises an aldonic acid or a derivative thereof as an active ingredient, and preferably the aforementioned equol production accelerating composition, wherein the aldonic acid or the derivative thereof is one or two or more members selected from the group consisting of lactobionic acid, a salt of lactobionic acid and lactobionolactone.

Also, the gist of the present invention resides in an agent for preventing and/or treating osteoporosis, which contains the aforementioned equol production accelerating composition, resides in a food or drink having a function to increase bone density, which comprises the aforementioned equol production accelerating composition, resides in a feed or a pet food having a function to increase bone density, which comprises the aforementioned equol production accelerating composition, resides in an agent for preventing breast cancer or prostatic cancer, which comprises the aforementioned equol production accelerating composition, resides in a food or drink having a function to prevent breast cancer or prostatic cancer, which comprises the aforementioned equol production accelerating composition, resides in an agent for lowering cholesterol, which comprises the aforementioned equol production accelerating composition, and resides in a food or drink having a function to lower cholesterol, which comprises the aforementioned equol production accelerating composition.

Further, the gist of the present invention also resides in use of an aldonic acid or a derivative thereof for the manufacture of an equol production accelerating composition, use of an aldonic acid or a derivative thereof for the manufacture of an agent for preventing or treating osteoporosis, use of an aldonic acid or a derivative thereof for the manufacture of a food or drink, a feed or a pet food having a function to increase bone density, use of an aldonic acid or a derivative thereof for the manufacture of an agent for preventing breast cancer or prostatic cancer or a food or drink having a function to prevent breast cancer or prostatic cancer, and use of an aldonic acid or a derivative thereof for the manufacture of an agent for lowering cholesterol or a food or drink having a function to lower cholesterol.

In addition, the gist of the present invention also resides in a method for accelerating equol production, which comprises administering an aldonic acid or a derivative thereof, a method for preventing or treating osteoporosis, which comprises administering an aldonic acid or a derivative thereof, a method for increasing bone density, which comprises administering an aldonic acid or a derivative thereof, a method for preventing breast cancer or prostatic cancer, which comprises administering an aldonic acid or a derivative thereof, and a method for lowering cholesterol, which comprises administering an aldonic acid or a derivative thereof.

Effect of the Invention

Since the equol production accelerating composition of the present invention has a markedly high equol production accelerating effect, it exerts effects for preventing a vascular disease by the cholesterol lowering function, preventing breast cancer or prostatic cancer and preventing and/or treating osteoporosis, when formulated in a pharmaceutical preparation or a food or drink. Also, when formulated in a feed or a pet food, bone density is enhanced so that it exerts effects to prevent weak legs of a pig, to strengthen egg shell of a laying hen, to prevent osteoporosis in a dog etc., and the like. In addition, when formulated in a food or drink and the like, the formulation designing becomes easy because the addition amount is low.

BRIEF DESCRIPTION OF THE DRAWINGS

FIG. 1 is a graph showing the equol concentration in blood plasma of rats to which samples were given for 5 weeks. Significant differences between the amounts are shown with different alphabets.

BEST MODE FOR CARRYING OUT THE INVENTION

The following describes the present invention in detail.

The aldonic acid in the present invention include not only those that the hemiacetal hydroxyl group of an aldose, which is a monosaccharide, is oxidized, but also include those that the hemiacetal hydroxyl group of a sugar of disaccharide or more having an aldose structure at the reducing terminal is oxidized. Of these, lactobionic acid, a salt of lactobionic acid or lactobionolactone is preferable as the active ingredient. As the salt, alkali metals such as sodium, potassium and the like, alkaline earth metals such as calcium and the like, magnesium, iron and the like can be considered. It is known that lactobionic acid forms a chelate when a salt is formed with polyvalent metals such as iron, magnesium, calcium or the like.

As the method for obtaining lactobionic acid according to this invention, it can be obtained by allowing a microorganism such as *Pseudomonas graveolens* or the like having lactose dehydrogenase activity using lactose as the substrate, or by oxidizing lactose with bromine or the like, but a method for obtaining it by oxidizing lactose using an oxidase which uses lactose as the substrate or a microorganism belonging to the genus *Acinetobacter*, the genus *Burkholderia* or the like having the enzyme is known (see JP-A-2001-245657 for details).

The salt of lactobionic acid used in the present invention can be prepared by a general salt conversion reaction such as neutralization of lactobionic acid, but a method in which calcium carbonate or the like is added in advance to a reaction system for producing lactobionic acid from lactose by a bioconversion reaction which uses an enzyme or a microorganism is convenient. The lactobionolactone can be easily obtained by subjecting lactobionic acid to intramolecular dehydration condensation using an acid catalyst.

The active ingredient prepared by the above method can be used as the equol production accelerating composition by itself or together with a solid or liquid excipient conventionally known in this field.

As the solid excipient, for example, lactose, sucrose, glucose, corn starch, gelatin and starch may be cited. Also, as the liquid excipient, for example, water, glycerin, fatty oil and sorbitol may be cited.

As occasion demands, the equol production accelerating composition of the present invention may contain other drugs such as, medicine for intestinal disorders such as, for example, berberine chloride, Phellodendron powder or the like, antibacterial agent such as, for example, oxytetracycline, bicozamycin or the like, antifungal agent such as, for example, sodium propionate or the like, vermicide such as, for example, praziquantel, ivermectin or the like and/or general additive agents such as an antioxidant, a pigment, a flavor, a gustatory agent, an enzyme and the like. Isoflavones may be added thereto in advance in order to further accelerate production of equol. It can be prepared into pharmaceutical preparations in the form of powders, granules, solutions, tablets and the like by general methods.

These compositions themselves can be administered to a human or an animal and also can be used as a medicine, a food or drink, a feed or a pet food. When used as a food or drink or a feed, it is convenient and preferable to use the compositions by adding them to the materials in advance.

The food or drink, feed or pet food to which the equol production accelerating composition of the present invention should be added are not particularly limited with the proviso that they are generally used ones. For example, the food or drink, feed or pet food which use soybean, albumen, milk, wheat flour, mackerel, shrimp and the like as the raw material can be cited.

As examples of such food or drink, health food in the form of tablets, powders, granules, syrups, capsules and the like, processed cereals such as breads, confectioneries, cookies, biscuits and the like, dairy products such as milk, yogurt, ice cream and the like, drinks such as a carbonated drink, a soft drink, a fruit juice-supplemented soft drink, a fruit juice-supplemented drink, a drug-type drink and the like, daily dishes and processed foods which use soybean, fish meat, meat etc., and the like may be cited.

Also, as examples of the feed and pet food, those which are prepared by optionally mixing corn, rice, wheat, milo, soy bean cake, wheat bran, defatted rice bran, fish meal, skim milk powder, dried whey, oil and fat, alfalfa meal, Hokuyo meal (white fish meal), soybean oil and fat, purified beef fat powder, wheat flour, rapeseed oil and fat, meat and bone meal (Feather Meal), animal oil and fat, calcium phosphate, corn gluten meal, molasses, corn germ meal, calcium carbonate, tricalcium phosphate, sodium chloride, choline chloride, vitamins (vitamin A, vitamin $B_1$, vitamin $B_2$, vitamin $B_6$, vitamin $B_{12}$, vitamin D, vitamin E, calcium pantothenate, nicotinamide, folic acid and the like), amino acids (lysine, methionine and the like), trace inorganic salts (magnesium sulfate, iron sulfate, copper sulfate, zinc sulfate, potassium iodide, cobalt sulfate and the like), probiotic agents and the like, may be cited.

In addition, as the pharmaceutical preparation, it may be ingested in the form of powders, tablets, granules, capsules, suspensions, syrups, liquids for internal use, troches and the like.

Though content of the equol production accelerating composition of the present invention depends on the kind, body weight and the like of the human or animal to be used as the object, in the case that the composition is used by adding to a food or drink, a feed or a pet food, the content is generally from 0.01 to 10.0% by weight, preferably from 0.01 to 5.0% by weight, as lactobionic acid, a salt of lactobionic acid or lactobionolactone. Also, when used as a pharmaceutical preparation, it is preferable to design the pharmaceutical preparation such that from 10 mg to 100 g, preferably from 100 mg to 10 g, more preferably from 1 g to 5 g, per day per 50 kg adult as lactobionic acid, a salt of lactobionic acid or lactobionolactone is ingested.

EXAMPLES

The following describes the present invention further in detail with reference to Examples, but the present invention is not limited to these Examples.

Example 1

Test for Confirming Equol Production Accelerating Effect of Calcium Lactobionate in Rats 1. Samples Calcium lactobionate (manufactured by Sigma Aldrich) was mixed with a rat powder feed (CRF-1, manufactured by Oriental Yeast Co., Ltd.) to a concentration of 0, 0.5 or 3.0% by weight. Also, as comparative controls, a 1.5% by weight difructose-dianhydride III (DFA-III) (manufactured by Wako Pure Chemical Industries, Ltd)-mixed powder feed and a 1.5% by weight fructo-oligosaccharide (FOS) (manufactured by Wako Pure Chemical Industries, Ltd)-mixed powder feed were used.

2. Experimental Animal and Rearing

Acclimatization rearing of 3 animals per group of 5-week-old SD rats (manufactured by Clea Japan, Inc.) was carried out for 1 week by allowing to freely ingest the powder feed CRF-1 and water. The time of completion of the acclimatization rearing was regarded as the week 0.1 Starting from the week 0, respective groups were allowed to freely ingest the calcium lactobionate-mixed powder feed prepared in the above. The control groups were allowed to ingest a general powder feed.

3. Measurement of Equol in Blood Plasma

The conjugated soybean isoflavone presenting in the rat blood plasma was converted into its free state using β-glucuronidase, and then equol was measured using an LC/MS/MS system. As the instruments for analysis, HP1100 Series, Agilent Technologies, was used in the LC, and Quattro-Ultima, Micromass was used in the MS/MS. As the reaction conditions, this was carried out at a linear gradient (flow rate at the peak elution: 0.2 mL/min), using a PEGASIL ODS 2 mm×150 mm column of Senshu Scientific Co., Ltd., keeping the column temperature at 40° C. and using purified water and methanol/acetonitrile (2:1) in the moving layer. Electro spray (−) was used in the ionization method.

4. Test Conditions

As the test groups, (1) control (general feed administration) group, (2) 0.5% by weight calcium lactobionate (LA)-mixed powder feed administration group, (3) 3.0% by weight calcium lactobionate-mixed powder feed administration group, (4) 1.5% by weight difructose-dianhydride III (DFA-III)-mixed powder feed administration group and (5) 1.5% by weight fructo-oligosaccharide (FOS)-mixed powder feed administration group were set. On the week 5, blood sample collection was carried out to prepare blood plasma and measure the equol concentration. 5. Test Results Results of the measurement of the equol concentration in blood plasma in each group are shown in FIG. 1. Specifically, there are differences (indicating the effects of accelerating equol production by lactobionic acid) between control (a), and 0.5% LA (b) and 3.0% LA (c). There is also a difference between control (a) and 1.5% DFA-III (d) (in this regard, 1.5% FOS (a, d) indicates that there is no difference with control (a) or with 1.5% DFA(d)). Further, there are significant differences between 0.5% LA (b) and 3.0% LA (c), and 1.5% DFA-III (d). Therefore, the composition of the present application is shown to have an effect of accelerating equol production as compared to known substances, i.e., DFA-III and FOS. As a result, in spite of the relatively short administration period of 5 weeks, significant increase in the equol concentration, which was 2 to 3 times of the control group, was observed by calcium lactobionate. In addition, it was also confirmed that the equol concentration was high compared to the DFA-III and fructo-oligosaccharide. Accordingly, it was suggested that production of equol in the intestines can be accelerated by continuously ingesting food or the like containing calcium lactobionate and, as a result, equol concentration in blood plasma can be increased.

While the present invention has been described in detail and with reference to specific embodiments thereof, it will be apparent to one skilled in the art that various changes and modifications can be made therein without departing from the spirit and scope of the present invention.

This application is based on a Japanese patent application filed on Jun. 20, 2006 (Japanese Patent Application No. 2006-170202), and the entire contents thereof being thereby incorporated by reference.

INDUSTRIAL APPLICABILITY

When the equol production accelerating composition of the present invention is used in a food or drink, a feed, a pharmaceutical preparation and the like, and ingested, effects such as acceleration of equol production in the intestines, improvement of bone density and the like are obtained.

The invention claimed is:

1. A method for treating breast cancer or prostatic cancer of a human or animal comprising administering to the human or animal in need of treatment an equol production accelerating composition, which comprises an aldonic acid or a derivative thereof as an active ingredient and an isoflavone, wherein the aldonic acid or the derivative thereof is one or more members selected from the group consisting of lactobionic acid, a salt of lactobionic acid and lactobionolactone, wherein the amount of the aldonic acid or derivative thereof is from 0.2 to 3% by weight, and wherein the aldonic acid or derivative thereof and the isoflavone are present in synergistically effective amounts, wherein the equol production accelerating composition is administered in an amount effective to increase the concentration of equol in the blood.

2. The method of claim 1, wherein said salt is an alkali metal salt, an alkaline earth metal salt, a magnesium salt or an iron salt.

3. The method of claim 1, wherein said active ingredient is administered in a food or drink.

4. The method of claim 1, wherein said active ingredient is administered in a feed or pet food.

* * * * *